United States Patent [19]

Tabushi et al.

[11] 4,229,356
[45] Oct. 21, 1980

[54] PRODUCTION OF VITAMIN K$_1$ AND VITAMIN K$_2$

[75] Inventors: Iwao Tabushi, Kyoto; Hiroyuki Sugimoto; Akira Yazaki, both of Hiroshima, all of Japan

[73] Assignee: Wakunaga Yakuhin Kabushiki Kaisha, Osaka, Japan

[21] Appl. No.: 15,868

[22] Filed: Feb. 27, 1979

[30] Foreign Application Priority Data

Mar. 4, 1978 [JP] Japan ................... 53-24057
Mar. 4, 1978 [JP] Japan ................... 53-24058

[51] Int. Cl.$^2$ ................... C07C 49/62; C07C 39/14
[52] U.S. Cl. ................... 260/396 K; 568/790; 568/766
[58] Field of Search ................... 260/396 K; 568/790, 568/766

[56] References Cited

U.S. PATENT DOCUMENTS

| | | | |
|---|---|---|---|
| 2,376,984 | 5/1945 | Tishler | 260/396 K |
| 2,831,899 | 4/1958 | Wendler | 260/396 K |
| 3,948,958 | 4/1976 | Rapoport et al. | 260/396 K |
| 3,992,432 | 11/1976 | Napier et al. | 260/465.1 |
| 4,089,873 | 5/1978 | Rapoport et al. | 260/396 K |

OTHER PUBLICATIONS

Fieser et al., J.A.C.S., vol. 61, pp. 3467–3475 (1939).
Sato et al., J. Chem. Soc., Perkin I, 1973, pp. 2289–2293.
Evans et al., J.A.C.S., vol. 98, pp. 1983–1984 (1976).
Snyder et al., J.A.C.S., vol. 96, pp. 8046–8054 (1974).
Yogi, Chem. Letters, pp. 901–902 (1977).
Naruta et al., Chem. Letters, pp. 881–884 (1979).

Tabushi, J.A.C.S., vol. 99, pp. 6456–6457 (1977).

*Primary Examiner*—Natalie Trousof
*Assistant Examiner*—James H. Reamer
*Attorney, Agent, or Firm*—Wenderoth, Lind & Ponack

[57] ABSTRACT

A process for producing hydro-precursors for vitamin K$_1$ and vitamin K$_2$ which comprises reacting (A) 2-methylhydronaphthoquinone-1,4 with (B) a compound selected from the group consisting of phytyl bromide, isophytyl bromide, geranyl bromide, farnesyl bromide, geranylgeranyl bromide and the corresponding chlorides in a reaction system which comprises an aqueous phase comprising an aqueous solution of an alkali and an oily phase comprising a hydrophobic organic solvent, in the presence of a salt comprising a quaternary ammonium ion or a tetraalkyl phosphonium ion represented by the formula (I) or formula (II):

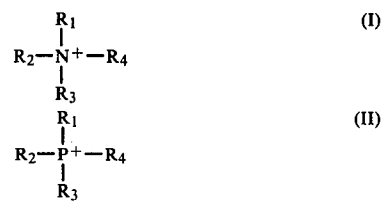

wherein R$_1$, R$_2$, R$_3$ and R$_4$ each represent an alkyl or aralkyl group containing from 1 to 20 carbon atoms and the sum of the carbons in R$_1$, R$_2$, R$_3$ and R$_4$ groups is at least 12. The resultant hydro-precursor is oxidized to convert it into vitamin K$_1$ or vitamin K$_2$.

10 Claims, No Drawings

PRODUCTION OF VITAMIN $K_1$ AND VITAMIN $K_2$

BACKGROUND OF THE INVENTION

The present invention relates to production of vitamin $K_1$ and vitamin $K_2$. More specifically, the present invention relates to a process for producing precursors for the above mentioned vitamins $K_1$ and $K_2$, which precursors are converted into the vitamins by oxidation, by alkylating 2-methylhydronaphthoquinone-1,4 with a specified alkylating agent.

Heretofore, it has been known that, in general, vitamin $K_1$ can be prepared by condensing 2-methylhydronaphthoquinone-1,4 with phytol, isophytol or derivatives thereof with heat in an organic solvent in the presence of an acid catalyst such as oxalic acid or boron trifluoride etherate to produce a hydroprecursor and oxidizing the hydro-precursor with an inorganic oxidizing agent such as manganese dioxide or silver oxide to convert it into vitamin $K_1$. However, a problem accompanying this process is that it provides a very low yield of vitamin $K_1$ because 2-methyl-2-phytyl-2,3-dihydronaphthoquinone-1,4 is produced as a by-product in a quantity approximately equal to that of vitamin $K_1$.

In order to overcome the above mentioned drawback, acylation has been carried out in the hydroxyl group of the 1-position to prevent the formation of the by-product. However, this process is accompanied by a problem in that the synthesis of 4-acyloxy-3-methyl-1-naphthol requires complicated procedures and provides a low yield, and the resulting condensation product must by hydrolysed with an alkali because it is in the form of a half ester. For the same purpose, there has also been proposed a process using 2-methyl-1,4-naphthohydroquinoneditetrahydro-pyranylether. In this process, the yield of vitamin $K_1$ is not very high in spite of the use of an expensive protective group 2,3-dihydropyran, and the dehydration of the solvent used and the purification of the catalyst used must be carefully carried out.

Additionally, it is known that vitamin $K_2$ (10) can be synthesized by condensing a monopotassium salt of 2-methylhydronaphthoquinone-1,4 with geranyl bromide with heat in toluene as a medium. This process requires complicated operations and, as in the case of the acid catalyst reaction, produces a by-product, 2-methyl-2-geranyl-2,3-dihydronaphthoquinone-1,4, with the result that the yield has is as low as 20%.

Moreover, there has been proposed a process comprising condensing a halide of 2-methyl-1,4-dialkoxynaphthalene in the presence of a $\pi$-allylnickel complex and a process comprising synthesizing metaloquinone from 2-methyl-1,4-dialkoxynaphthalene and condensing the metaloquinone with an allyl halide. All these synthetic processes entail a large number of steps and require the absence of water, thereby requiring accurate control of operations.

SUMMARY OF THE INVENTION

It is an object of the present invention to provide a process for producing vitamin $K_1$ or $K_2$ which is free of the problems accompanying the above described prior art.

In the process of the present invention 2-methylhydronaphthoquinone-1,4 is used as a source of a naphthoquinone structure or skeleton for vitamin $K_1$ or $K_2$ and 3-position thereof is alkylated to form a hydroprecursor for vitamin $K_1$ or $K_2$, wherein the alkylation is carried out in a two-phase reaction system consisting of an aqueous solution of an alkali and a hydrophobic organic solvent in the presence of a quaternary ammonium or tetraalkyl phosphonium salt.

Accordingly, the process for producing hydroprecursors for vitamin $K_1$ and vitamin $K_2$ according to the present invention comprises reacting (A) 2-methylhydronaphthoquinone-1,4 with (B) a compound selected from the group consisting of phytyl bromide, isophytyl bromide, geranyl bromide, farnesyl bromide, geranylgeranyl bromide, and corresponding chlorides in a reaction system which comprises an aqueous phase comprising an aqueous solution of an alkali and an oily phase comprising a hydrophobic organic solvent, in the presence of a salt comprising a quaternary ammonium ion or a tetraalkyl phosphonium ion represented by the formula (I) or (II):

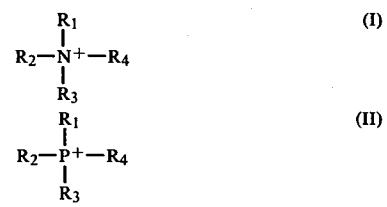

wherein each of $R_1$, $R_2$, $R_3$ and $R_4$ represents an alkyl or aralkyl group containing from 1 to 20 carbon atoms and the sum of the carbon atoms in $R_1$, $R_2$, $R_3$ and $R_4$ groups is at least 12.

Upon oxidation of the hydro-precursor, a naphthoquinone structure is completed, so that vitamin $K_1$ or vitamin $K_2$ is formed.

DETAILED DESCRIPTION OF THE INVENTION

Reactant

The starting material compounds used in the process of the present invention are (A) 2-methylhydronaphthoquinone-1,4 and (B) a compound selected from the group consisting of phytyl bromide, isophytyl bromide, geranyl bromide, farnesyl bromide, geranylgeranyl bromide and the corresponding chlorides. In this case, the compound (A), i.e., 2-methylhydronaphthoquinone-1,4 is always used, but the compound (B) is selected in accordance with the type of the vitamin to be prepared. When vitamin $K_1$ is to be prepared, phytyl bromide or isophytyl bromide is used as the compound (B). When vitamin $K_2$(10) is to be prepared, geranyl bromide is used. When vitamin $K_2$(15) and $K_2$(20) are to be prepared, farnesyl bromide and geranylgeranyl bromide are respectively used. The chlorides are usable, but the bromides are preferable.

The quantities of the compound (A) and compound (B) used are not particularly critical, and from the theoretical point of view they may be used in an equimolar ratio. However, it is ordinarily preferable that the compound (A) be used in a proportion of 1 to 5 equivalents relative to the compound (B).

Reaction system

The reaction system in which the reaction of the reactants (A) and (B) is carried out comprises two heterogeneous phases, that is, (1) aqueous phase comprising an aqueous solution of an alkali and (2) an oily phase comprising a hydrophobic organic solvent.

In the reaction according to the present invention, material transfer between these two phases is considered to possess a certain significance as described hereinafter, although we are not bound to such a theory. Accordingly, it is desirable that the two phases be not merely present as layers, but, rather, that one of the phases be dispersed in the other phase. Therefore, it is preferable that the reaction system consisting of the two phases be under sufficient agitation. This reaction system contains a quaternary ammonium salt or a tetraalkyl phosphonium salt which may have some surface activity. Accordingly, when the two-phase reaction system is well stirred, an emulsion is usually formed.

The hydrophobic organic solvent used in the present invention should be hydrophobic to such an extent that it is able to form an oily phase relative to an aqueous alkali solution. In the reaction system of the present invention, the hydrophobic organic solvent should also dissolve the resulting hydroprecursor for vitamin $K_1$ or $K_2$ at least partially or to a desirable extent.

As long as such conditions are satisfied, any of various organic solvents may be used. Examples of these solvents are hydrocarbons, particularly aromatic hydrocarbons, such as pentane, hexane, benzene, toluene and xylene; halo-hydrocarbons such as chloroform, methylene chloride, 1,2-dichloroethane and monochlorobenzene; ethers such as diethyl ether and, anisole; and esters such as ethyl acetate, butyl acetate and ethyl benzoate. Among these, chloroform, methylene chloride, 1,2-dichloroethane, diethyl ether, ethyl acetate, benzene, toluene and xylene are preferable.

The aqueous alkali solution which comprises the other phase of the two phase reaction system of the present invention may be an aqueous solution of any suitable water-soluble alkali. The most typical examples of such water-soluble alkalis are hydroxides, carbonates and borates of alkali metals, particularly sodium and potassium. An inorganic alkali is generally suitable. Typical examples are an aqueous solution of sodium hydroxide or potassium hydroxide. The concentration and quantity of the aqueous alkali solution depend on various conditions and can not be simply determined. However, it is preferable that the concentration and quantity be adjusted in such a manner that the pH of the reaction system, i.e. the pH of the aqueous phase, ranges from 9 to 14, preferably around 14. Ordinarily, the aqueous alkali solution is added in a quantity of 1 to 100 parts by volume relative to 100 parts by volume of the above mentioned organic solvent, and, when the resulting mixture is well stirred an, emulsion is formed.

Quaternary ammonium salt

The salt containing the quaternary ammonium ion represented by the formula (I) which may be used in the reaction system according to the present invention is one which functions as a catalyst migrating between the two phases. If a salt containing the above mentioned quaternary ammonium ion is not used in the reaction of the present invention, by-products such as 2-methyl-2-phytyl-2,3-dihydronaphthoquinone-1,4 and 2-methyl-2-geranyl-2,3-dihydronaphthoquinone-1,4 are formed in a quantity two or more times that of vitamin $K_1$ or vitamin $K_2$, thereby giving rise to a very poor yield. In contrast, when a salt containing the above mentioned quaternary ammonium ion is used as in the process of the present invention, the reaction rapidly proceeds while the above by-products are prevented from being produced and, as a result, vitamin $K_1$ or vitamin $K_2$ is obtained in a high yield. The reason for this is considered to be as follows.

When a salt containing the above quaternary ammonium ion is present in the reaction system, the anion of this salt (e.g., halide ion) is exchanged with the anion of 2-methylhydronaphthoquinone-1,4 formed in the aqueous alkali solution, and, as a result, the anion of 2-methylhydronaphthoquinone-1,4 migrates into the organic solvent phase as a counter ion for the quaternary ammonium ion. For this reason, the anion of 2-methylhydronaphthoquinone-1,4 formed in the aqueous phase rapidly reacts with phytyl bromide, isophytyl bromide, geranyl bromide, farnesyl bromide or geranylgeranyl bromide which is hydrophobic in nature in the organic solvent phase, whereby a high yield of vitamin $K_1$ or vitamin $K_2$ is obtained.

As a salt containing the quaternary ammonium ion represented by the formula (I) which functions as a catalyst migrating between the two phases which serves to rapidly transfer the anion of 2-methylhydronaphthoquinone-1,4 from the aqueous alkali solution phase to the organic solvent phase as described above, various salts may be used. Specific examples of suitable salts include trioctylmethylammonium salts such as trioctylmethylammonium chloride, tetrabutylammonium salts such as tetrabutylammonium bromide, and benzyltriethylammonium salts such as benzyltriethylammonium bromide. Other examples are hexyltriethylammonium bromide, octyltriethylammonium bromide, decyltriethylammonium bromide, dodecyltriethylammonium bromide, and cetyltrimethylammonium bromide.

In addition to halides such as chlorides and bromides as described above, hydrogen sulfate, nitrate, acetate, etc. may form the anion moiety of the quaternary ammonium salt.

In the process of the present invention, the quantity of the salt containing the above mentioned quaternary ammonium ion to be added is not particularly critical, and it may be suitably selected in accordance with various conditions. However, it is preferable that the salt be ordinarily added in a quantity of 1/20 to 1 equivalent, more preferably 1/15 to 1/5 equivalent, relative to the compound (B).

Tetraalkyl phosphonium salt

The tetraalkyl phosphonium salts which may be used in the reaction system according to the present invention have the cationic moiety represented by the formula (II).

Description of the quaternary ammonium salts given hereinabove is applicable also to the tetraalkyl phosphonium salts except for the specific examples.

Specific examples of the tetraalkyl phosphonium salts include tetrabutylphosphonium salts such as tetrabutylphosphonium chloride and tetrabutylphosphonium bromide; trioctylmethylphosphonium salts such as trioctylmethylphosphonium bromide; trioctylethylphosphonium salts such as trioctylethylphosphonium bromide.

Alkylation

In the practice of the process of the present invention, the reaction wherein the compound (A) is alkylated by the compound (B) may be allowed to proceed by using the above mentioned materials, catalysts and solvents preferably under stirring. It is desirable, however, that the reaction vessel be purged with an inert gas such as nitrogen and argon in order to prevent unnecessary oxidation during the reaction. The reaction temperature is not particularly critical, but a temperature of 10 to 80°

C., preferably 30 to 60° C., produces particularly desirable results. The reaction time may be 30 minutes to 30 hours, preferably 1 to 20 hours.

Oxidation

As described above, the product obtained by alkylating the compound A with the compound B is a hydro-precursor for vitamin $K_1$ or vitamin $K_2$. Oxidation of the hydro-precursor results in vitamin $K_1$ or vitamin $K_2$.

This oxidation can be carried out by any suitable process which may be used in the oxidation of hydronaphthoquinone. In this case, care should be taken so that the moiety which contains unsaturation, and which has been introduced into the hydro-precursor from the compound (B), is not oxidized.

An example of this oxidation is a chemical oxidation with an oxide such as silver oxide and manganese dioxide. Another example of the oxidation is an air oxidation. The chemical oxidation proceeds with relative ease. For example, it may be carried out by contacting silver oxide with the hydro-precursor at a temperature of about 0° C. to 60° C., preferably 20 to 40° C., for about 10 minutes to 60 minutes, preferably 15 to 30 minutes. Examples of oxidation with silver oxide are found in Clinton, Snyder and Rapoport: J.Am. Chem. Soc. Vol. 96, 8046 (1974) and Tabushi, Fujita and Kawakubo: J. Am. Chem. Soc. Vol. 99, 6456 (1977).

Air oxidation may be carried out by blowing or bubbling air into a solution of the hydro-precursor at a temperature of 0° to 80° C., preferably 20° to 30° C., for 5 to 30 hours, preferably 15 to 25 hours.

As described above, in accordance with the present invention, the condensation reaction between the compound (A) and the compound (B) rapidly proceeds, resulting in highly pure vitamin $K_1$ or vitamin $K_2$ in a high yield.

In order to indicate more fully the nature and utility of this invention, the following specific examples of practice are set forth, it being understood that these examples are presented as illustrative only and that they are not intended to limit the scope of the invention.

EXAMPLE 1

10 g of phytyl bromide, 15 g of 2-methylhydronaphthoquinone-1,4, and 3 g of trioctylmethylammonium chloride were added to 300 ml of chloroform contained in a reaction vessel, and 10 ml of a 20% aqueous solution of sodium hydroxide was then added to the reaction vessel, the atmosphere inside the vessel being replaced with argon. The resulting mixture was heated to a temperature of 60° C. and vigorously stirred at that temperature for 30 minutes. After the reaction was complete, the reaction mixture was cooled to room temperature and acidified with the addition of 100 ml of 5% hydrochloric acid.

Then, the resultant mixture was stirred for 10 minutes and the chloroform layer was separated. The chloroform layer was then washed twice with 100 ml portions of water and dried over Glauber's salt. Thereafter, 20 g of silver oxide was added to the as-dried material, and the mixture was stirred for 15 minutes to oxidize the material. The resultant oxidation mixture was filtered, and the solvent was distilled off. The residue was purified on 800 g of silica gel by chromatography (eluent, petroleum ether:ethyl acetate=15:1) to obtain 6.4 g (51%) of vitamin $K_1$.

The purified product had an extinction coefficient $E_1$ $cm^{1\%}=419$ (248 nm, in isooctane) and an infrared absorption spectrum coinciding with the infrared absorption spectrum of a sample of vitamin $K_1$ synthesized by a known process.

EXAMPLE 2

5.6 g (yield 45%) of vitamin $K_1$ was obtained in the manner described in Example 1 except that the reaction temperature was room temperature and the reaction time was 4 hours.

EXAMPLE 3

4.1 g (yield 33%) of vitamin $K_1$ was obtained in the manner described in Example 1 except that 2.5 g of tetrabutylammonium bromide was used instead of trioctylmethylammonium chloride.

EXAMPLE 4

4.1 g (yield 33%) of vitamin $K_1$ was obtained in the manner described in Example 1 except that 300 ml of 1,2-dichloroethane was used instead of chloroform, and the reaction temperature was 80° C.

EXAMPLE 5

3.3 g (yield 27%) of vitamin $K_1$ was obtained in the manner described in Example 1 except that 300 ml of benzene was used instead of chloroform, and the reaction temperature was 80° C.

EXAMPLE 6

5.5 g (yield 44%) of vitamin $K_1$ was obtained in the manner described in Example 1 except that 10 g of isophytyl bromide was used instead of phytyl bromide.

EXAMPLE 7

6 g of geranyl bromide, 15 g of 2-methylhydronaphthoquinone-1,4, and 3 g of trioctylmethyl ammonium chloride were added to 300 ml of chloroform contained in a reaction vessel, and 50 ml of a 4% aqueous solution of sodium hydroxide was then added to the reaction vessel, the atmosphere inside the vessel being replaced with argon. The resulting mixture was heated to a temperature of 60° C. and vigorously stirred at that temperature for 30 minutes. After the reaction was complete, the resultant mixture was cooled to room temperature and acidified with 100 ml of 5% hydrochloric acid.

The mixture was then stirred for 10 minutes and the chloroform layer was separated. The chloroform layer was washed twice with 100 ml portions of water and dried over Glauber's salt. 20 g of silver oxide was then added to the as-dried material, and the mixture was stirred for 15 minutes to oxidize the material. The resultant oxidation mixture was filtered, and the solvent was distilled off. The residue was purified on 600 g of silica gel by chromatography (eluent, petroleum ether: ethyl acetate=15:1) to obtain 2.5 g (yield 30%) of vitamin $K_2$ (10).

The purified product had an absorption peak at 2940 $cm^{-1}$, 1660 $cm^{-1}$, 1620$cm^{-1}$, 1595 $cm^{-1}$, 1440 $cm^{-1}$, 1380 $cm^{-1}$, and 1300 $cm^{-1}$ by infrared absorption spectrum analysis, which coincided with the infrared absorption spectrum of a sample of vitamin $K_2$ (10) synthesized by a known process.

EXAMPLE 8

10 g of phytyl bromide, 15 g of 2-methylhydronaphthoquinone-1,4, and 3 g of tetrabutyl phosphonium bromide were added to 300 ml of chloroform contained in a reaction vessel, and 10 ml of a 20% aqueous solution of sodium hydroxide was then added to the reaction vessel, the atmosphere inside the vessel being replaced with argon. The resulting mixture was heated to a temperature of 60° C. and vigorously stirred at that temperature for 30 minutes. After the reaction was complete, the reaction mixture was cooled to room temperature and acidified with the addition of 100 ml of 5% hydrochloric acid.

Then, the resultant mixture was stirred for 10 minutes and the chloroform layer was separated. The chloroform layer was then washed twice with 100 ml portions of water and dried over Glauber's salt. Thereafter, 20 g of silver oxide was added to the as-dried material, and the mixture was stirred for 15 minutes to oxidize the material. The resultant oxidation mixture was filtered, and the solvent was distilled off. The residue was purified on 800 g of silica gel by chromatography (eluent, petroleum ether:ethyl acetate=15:1) to obtain 4.3 g (34%) of vitamin $K_1$.

The purified product had an extinction coefficient $E_1$ $cm^{1\%}$=419 (248 nm, in isooctane) and an infrared absorption spectrum coinciding with the infrared absorption spectrum of a sample of vitamin $K_1$ synthesized by a known process.

In the tetraalkylphosphonium salts, the $R_1$, $R_2$, $R_3$ and $R_4$ are preferably alkyls.

What is claimed is:

1. A process for producing a hydro-precursor for vitamin $K_1$ or vitamin $K_2$ which comprises reacting (A) 2-methylhydronaphthoquinone-1,4 with (B) a compound selected from the group consisting of phytyl bromide, isophytyl bromide, geranyl bromide, farnesyl bromide, geranylgeranyl bromide and the corresponding chlorides in a reaction system which comprises an emulsion of (1) an aqueous phase comprising an aqueous solution of an alkali based on an alkali metal and (2) an oily phase comprising a hydrophobic organic solvent which is able to at least partially dissolve said hydro-precursor, said reaction being carried out in the presence of at least a catalytic quantity of a salt having a quaternary ammonium ion represented by the formula (I) or a tetraalkyl phosphonium ion represented by the formula (II):

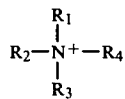
(I)

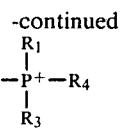
(II)

wherein $R_1$, $R_2$, $R_3$ and $R_4$ each represent an alkyl or aralkyl group containing from 1 to 20 carbon atoms and the sum of the number of carbon atoms in $R_1$, $R_2$, $R_3$ and $R_4$ is at least 12, the anion of said salt being a halide, hydrogen sulfate, nitrate or acetate, said reaction being carried out under conditions which result in production of said hydro-precursor, said hydroprecursor being 2-methylhydronaphthoquinone-1,4 whose 3-position is substituted by phytyl, isophytyl, geranyl, farnesyl or geranylgeranyl.

2. A process for producing vitamin $K_1$ or vitamin $K_2$ which comprises carrying out the process of claim 1 to obtain said hydro-precursor, and subjecting said hydroprecursor to chemical oxidation or air oxidation under conditions which result in converting the 2-methylhydronaphthoquinone-1,4 moiety of said hydro-precursor to a 2-methylnaphthoquinone-1,4 moiety.

3. A process as claimed in claim 1, wherein the quaternary ammonium ion is a member selected from the group consisting of trioctylmethylammonium ion, tetrabutylammonium ion, benzyltriethylammonium ion, hexyltriethylammonium ion, octyltriethylammonium ion, decyltriethylammonium ion, dodecyltriethylammonium ion, and cetyltrimethylammonium ion.

4. A process as claimed in claim 1, wherein the hydrophobic organic solvent is a member selected from the group consisting of chloroform, methylene chloride, 1,2-dichloroethane, diethyl ether, ethyl acetate, and benzene.

5. A process as claimed in claim 1, wherein the aqueous phase has a pH of 9 to 14.

6. A process as claimed in any one of claims 3, 4, 5, 1 or 2 wherein the compound (B) is selected from the group consisting of phytyl bromide and isophytyl bromide and the hydro-precursor is for vitamin $K_1$.

7. A process as claimed in any one of claims 3, 4, 5, 1 or 2 wherein the compound (B) is geranyl bromide and the hydro-precursor is for vitamin $K_2(10)$.

8. A process as claimed in any one of claims 3, 4, 5, 1 or 2 wherein the compound (B) is farnesyl bromide or geranylgeranyl bromide and the hydro-precursor is for vitamin $K_2$ (15) or vitamin $K_2(20)$, respectively.

9. A process as claimed in any one of claims 3, 4, 5, 1 or 2 wherein the salt has the quaternary ammonium ion.

10. A process as claimed in any one of claims 3, 4, 5, 1 or 2, wherein the salt has the tetraalkylphosphonium ion.